United States Patent
Sharma et al.

(10) Patent No.: US 8,807,540 B2
(45) Date of Patent: Aug. 19, 2014

(54) FAN-BASED VOLATILE MATERIAL DISPENSING SYSTEM

(75) Inventors: Nitin Sharma, Kenosha, WI (US); Michael J. McGlade, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 289 days.

(21) Appl. No.: 13/494,903

(22) Filed: Jun. 12, 2012

(65) Prior Publication Data
US 2013/0328223 A1 Dec. 12, 2013

(51) Int. Cl.
*B01F 3/04* (2006.01)

(52) U.S. Cl.
USPC .................. 261/104; 261/DIG. 88; 239/44

(58) Field of Classification Search
USPC ........... 261/101, 104, 107, DIG. 88, DIG. 89; 239/44, 45
See application file for complete search history.

(56) References Cited

U.S. PATENT DOCUMENTS

| | | | |
|---|---|---|---|
| 2,283,028 A | 5/1942 | Bailey | |
| 3,706,401 A | 12/1972 | Gach | |
| 3,747,807 A | 7/1973 | Gach | |
| 3,747,902 A | 7/1973 | Bailey | |
| 3,829,071 A | 8/1974 | Valbona et al. | |
| 3,915,348 A | 10/1975 | Suhr | |
| 4,035,451 A | 7/1977 | Tringali | |
| 4,064,203 A | 12/1977 | Cox | |
| 4,166,087 A | 8/1979 | Cline et al. | |
| 4,271,092 A | 6/1981 | Sullivan et al. | |
| 4,383,951 A | 5/1983 | Palson | |
| 4,396,557 A | 8/1983 | DeLuca | |
| 4,432,938 A | 2/1984 | Meetze, Jr. | |
| 4,707,338 A | 11/1987 | Spector | |
| 4,739,928 A | 4/1988 | O'Neil | |
| 4,752,020 A | 6/1988 | Grueter et al. | |
| 5,356,043 A | 10/1994 | Glynn | |
| 5,480,591 A | 1/1996 | Lagneaux et al. | |
| 5,498,397 A | 3/1996 | Horng | |
| 5,662,835 A | 9/1997 | Collingwood | |
| 5,970,643 A | 10/1999 | Gawel, Jr. | |
| 6,371,450 B1 | 4/2002 | Davis et al. | |
| 6,569,387 B1 | 5/2003 | Furner et al. | |
| 6,610,254 B1 | 8/2003 | Furner et al. | |
| 6,632,405 B2 | 10/2003 | Lua | |

(Continued)

FOREIGN PATENT DOCUMENTS

EP 0496460 7/1992
JP 2011032927 2/2011

(Continued)

OTHER PUBLICATIONS

PCT/US2013/045326 International Search Report dated Nov. 12, 2013.

*Primary Examiner* — Robert A Hopkins (57) ABSTRACT

A volatile material dispensing system includes a housing and a refill unit. The refill unit includes a volatile material and a wicking surface. A fan is disposed within the housing. During an active state the fan draws ambient air into the housing and over the wicking surface, which is angled between about 20 degrees to about 75 degrees relative to a central axis of the housing. Further, during the active state the drawn air is expelled from the housing through channels of the fan at an angle of between about 20 degrees to about 75 degrees relative to the central axis of the housing.

20 Claims, 8 Drawing Sheets

(56) References Cited

U.S. PATENT DOCUMENTS

| | | |
|---|---|---|
| 6,713,024 B1 | 3/2004 | Arnell et al. |
| 6,769,631 B2 | 8/2004 | Brown |
| 6,957,012 B2 | 10/2005 | He et al. |
| 7,040,548 B2 | 5/2006 | Rodgers |
| 7,040,561 B2 | 5/2006 | Wong et al. |
| 7,157,057 B2 | 1/2007 | Gohil |
| 7,167,641 B2 | 1/2007 | Tam et al. |
| 7,175,815 B2 | 2/2007 | Yamasaki et al. |
| 7,341,698 B2 | 3/2008 | Pedrotti et al. |
| 7,382,975 B2 | 6/2008 | Caserta et al. |
| 7,484,675 B2 | 2/2009 | Brown |
| 7,499,632 B2 | 3/2009 | Granger et al. |
| 7,744,833 B2 | 6/2010 | Varanasi et al. |
| 7,748,687 B2 | 7/2010 | Pankhurst et al. |
| 7,840,123 B2 | 11/2010 | Belongia et al. |
| 7,857,236 B2 | 12/2010 | Zlotnik et al. |
| 7,887,759 B2 | 2/2011 | Triplett |
| 8,005,350 B2 | 8/2011 | Zlotnik et al. |
| 8,517,351 B2 * | 8/2013 | Sharma ............... 261/83 |
| 2003/0168473 A1 | 9/2003 | Ho |
| 2006/0043619 A1 | 3/2006 | Brown et al. |
| 2006/0163376 A1 | 7/2006 | Lakatos et al. |
| 2006/0233538 A1 | 10/2006 | Tollens et al. |
| 2007/0001024 A1 | 1/2007 | Wold et al. |
| 2007/0158456 A1 | 7/2007 | Spector |
| 2007/0210101 A1 | 9/2007 | Hammond et al. |
| 2007/0257130 A1 | 11/2007 | Butler et al. |
| 2011/0027124 A1 | 2/2011 | Albee et al. |
| 2011/0139890 A1 | 6/2011 | Soldan et al. |
| 2012/0012667 A1 | 1/2012 | Gasper et al. |
| 2012/0024975 A1 | 2/2012 | Sharma et al. |

FOREIGN PATENT DOCUMENTS

| | | |
|---|---|---|
| WO | 2007/142851 A2 | 12/2007 |
| WO | 2008001460 | 3/2008 |
| WO | 2010/019505 A1 | 2/2010 |
| WO | 2012149114 | 11/2012 |

* cited by examiner

FAN-BASED VOLATILE MATERIAL DISPENSING SYSTEM

CROSS REFERENCE TO RELATED APPLICATIONS

None.

REFERENCE REGARDING FEDERALLY SPONSORED RESEARCH OR DEVELOPMENT

Not applicable.

SEQUENTIAL LISTING

Not applicable.

BACKGROUND OF THE DISCLOSURE

1. Field of the Disclosure

The present disclosure relates to a volatile material dispensing system having a fan adapted to facilitate the emission of a volatile material from a wicking surface, and in particular, to a volatile material dispensing system having a mixed flow fan that pulls ambient air into the system and expels the air therefrom at angles selected to increase the energy efficiency of the fan while maintaining an appropriate level of volatile material disposed in the air.

2. Description of the Background of the Disclosure

Various volatile material dispensing devices are known in the prior art that generally comprise a reservoir that holds the volatile material and optionally include a housing to retain the reservoir. The prior art volatile material dispensing devices either allow passive diffusion of the volatile material to occur without the aid of a dispensing mechanism or enhance and/or facilitate the release of the volatile material using a dispensing mechanism. Typical dispensing mechanisms used in volatile material dispensing devices include a heating apparatus and/or a fan that either heats and/or supplies air, respectively, to the volatile material to facilitate the diffusion thereof.

Both passive dispensing devices and heat-based diffusion systems suffer from numerous drawbacks. In particular, supplying a heating mechanism, such as a heater, in a volatile material dispensing system elevates the temperature of the volatile material, which in turn, increases the diffusion intensity and oxidation of the volatile material. Oxidation may not be desired because it may cause the volatile material to smell and/or the color to be altered in an unpleasant way. Another drawback in heat-based diffusion systems is the occurrence of condensation that may occur inside of the system during use.

With respect to passive diffusion devices, emission of the volatile material may be affected by environmental factors, such as temperature, drafts in the environment surrounding the device, the type of volatile material and the like. Passive diffusion devices suffer from further drawbacks because such devices typically require a larger diffusion surface area of the reservoir to permit a sufficient amount of volatile material to be emitted into the surrounding atmosphere such that a consumer is able to detect the presence of the volatile material. Similarly, a larger device housing may be necessary to enclose and/or support the larger reservoir.

Both passive and heat-based diffusion systems suffer from limited diffusion capabilities. In particular, diffusion of the volatile material is typically restricted to the atmosphere immediately adjacent and surrounding the systems unless an outside force, such as a fan, acts to circulate the volatile material in the surrounding atmosphere. As such, fan-based systems have been utilized to facilitate diffusion of the volatile material. However, fan-based systems typically suffer from numerous drawbacks as well. For example, fan-based systems tend to have larger, unwieldy housings to enclose the fans. The use of fans also typically increases the power consumption of the diffusion device.

One type of fan-based system incorporates a centrifugal fan to assist in circulating the volatile-material laden air. Centrifugal fans typically change the direction of airflow after the air enters into the system and expel the air in a radial direction. However, such fan-based systems suffer from various obstacles because of the unique airflow pattern created. In particular, air is drawn into the housing and expelled through outlets or vents that are disposed at a 90 degree angle from the entry point. The vent location may be inconvenient, unsightly, and inefficient in terms of airflow through the system. Further, the vents may be disposed in an area of the housing such that the volatile material is dispersed in a substantially vertical manner or substantially horizontal manner with respect to the housing. Dispersion in both strictly horizontal and vertical manners limits the radius of detection of volatile material laden air. The radius of detection is defined as the radius around the volatile material dispenser by which a typical consumer can detect the volatile material laden air through the sense of smell. For example, volatile material laden air dispensed through a vent in a vertical direction typically includes a small radius of detection because the volatile material laden air dissipates in the area directly adjacent the housing. Similarly, volatile material laden air dispensed through a vent in a horizontal direction also typically includes a small radius of detection because the volatile material laden air contacts the ground or a support surface prior to widespread dispersion.

In contrast, the volatile material dispensing systems of the present invention leverage an efficient airflow pattern in conjunction with a mixed flow fan and vent placement, which expels volatile material laden air at specifically selected angles to maximize the radius of detection of the volatile material. The system further includes a refill unit having a wicking surface that allows volatile material to be mixed with ambient air without substantially impeding the air flow. The present disclosure provides new and non-obvious volatile material dispensing systems, which address one or more of the above issues.

SUMMARY OF THE INVENTION

According to one aspect of the invention, a volatile material dispensing system includes a housing and a refill unit. The refill unit includes a volatile material and a wicking surface. A fan is disposed within the housing. During an active state the fan draws ambient air into the housing and over the wicking surface, which is angled between about 20 degrees to about 75 degrees relative to a central axis of the housing. Further, during the active state the drawn air is expelled from the housing through channels of the fan at an angle of between about 20 degrees and about 75 degrees relative to the central axis of the housing.

According to another aspect of the invention, a refill unit for a volatile material dispensing system includes a reservoir for holding a volatile material and a wicking surface having a first upper angled section and a secondary wicking surface extending downwardly therefrom into the reservoir. The upper angled section is angled from between about 20 degrees to about 75 degrees from a central axis of the reservoir and the secondary wicking surface is substantially parallel to the central axis of the reservoir.

According to a different aspect of the invention, a refill unit for a volatile material dispensing system includes a base having a sidewall and a top plate. A reservoir within the base contains a volatile material. At least two opposing grooves are provided within the sidewall, wherein portions of the sidewall defining the grooves include an overhang portion for snap-fit receipt within a housing. A wicking surface includes a first wicking section angled with respect to a secondary wicking section in fluid communication with the reservoir.

DETAILED DESCRIPTION OF THE DRAWINGS

As best seen in FIGS. 1-4, a volatile material dispensing system 100 comprises a substantially cylindrical housing 102 with a plurality of openings disposed therein. The plurality of openings are provided as elongate lower openings 104a and upper vents 104b. The housing 102 comprises four elongate, bowed support members 106 and a cylindrical sidewall 108 supported thereby. The support members 106 terminate at a slightly convex circular end cap 110 disposed on an upper end 112 of the housing 102. The end cap 110 acts to enclose the upper end 112 of the housing 102. In a different embodiment, the housing 102 comprises other shapes and, sizes, for example, square, rectangular, oval, and the like.

Figure 1:
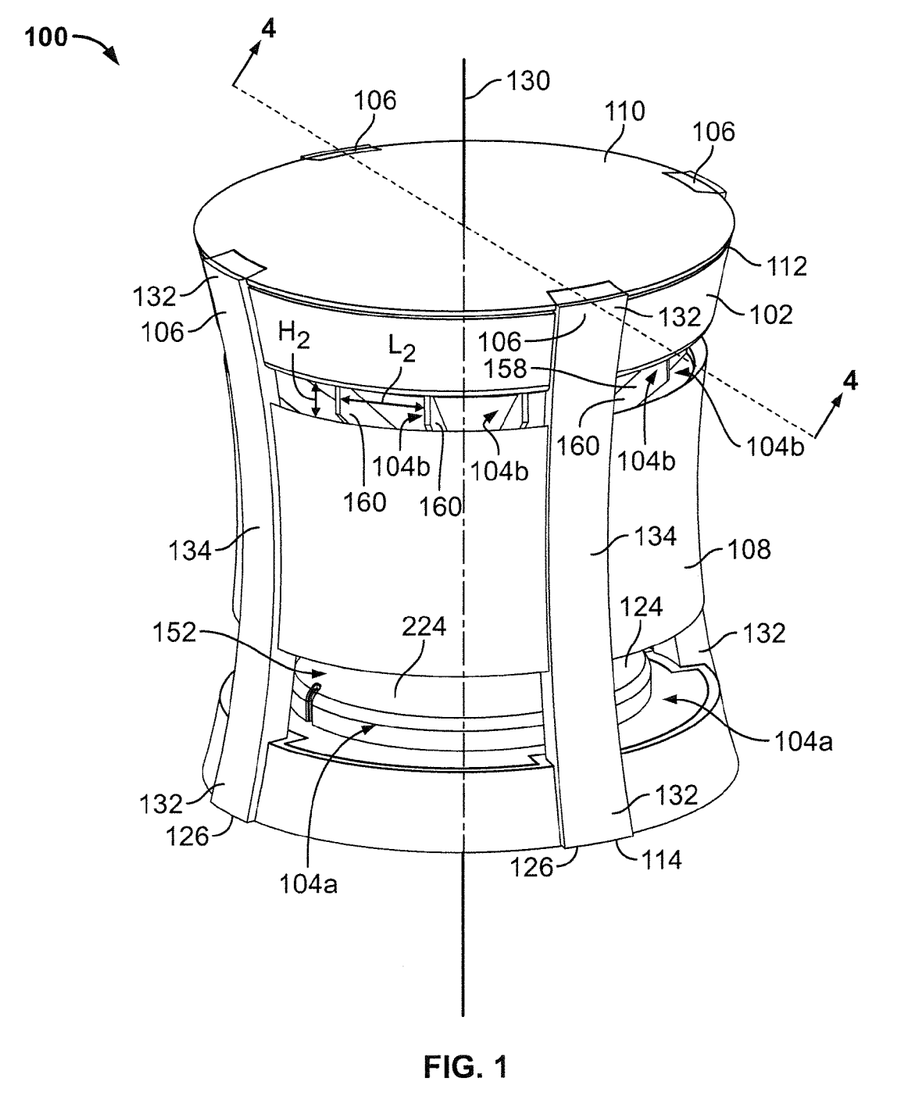
FIG. 1 is an isometric view of a top, front, and side of a volatile material dispensing system that includes a housing and a refill unit disposed therein.
Figure 2:
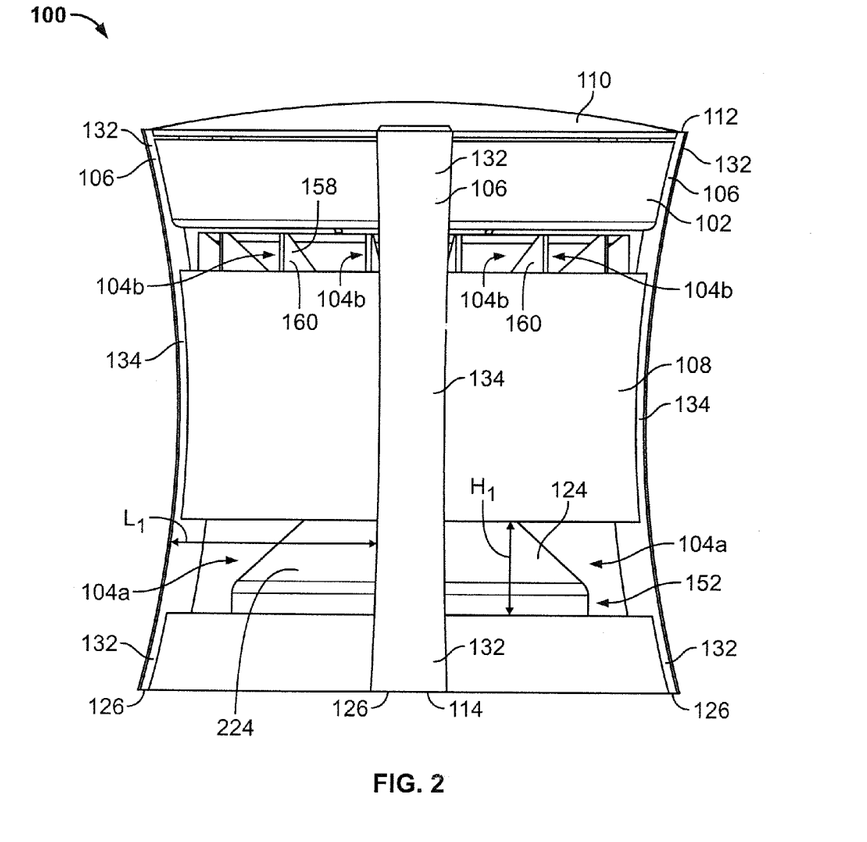
FIG. 2 is a side elevational view of the dispensing system of FIG. 1.
Figure 3:
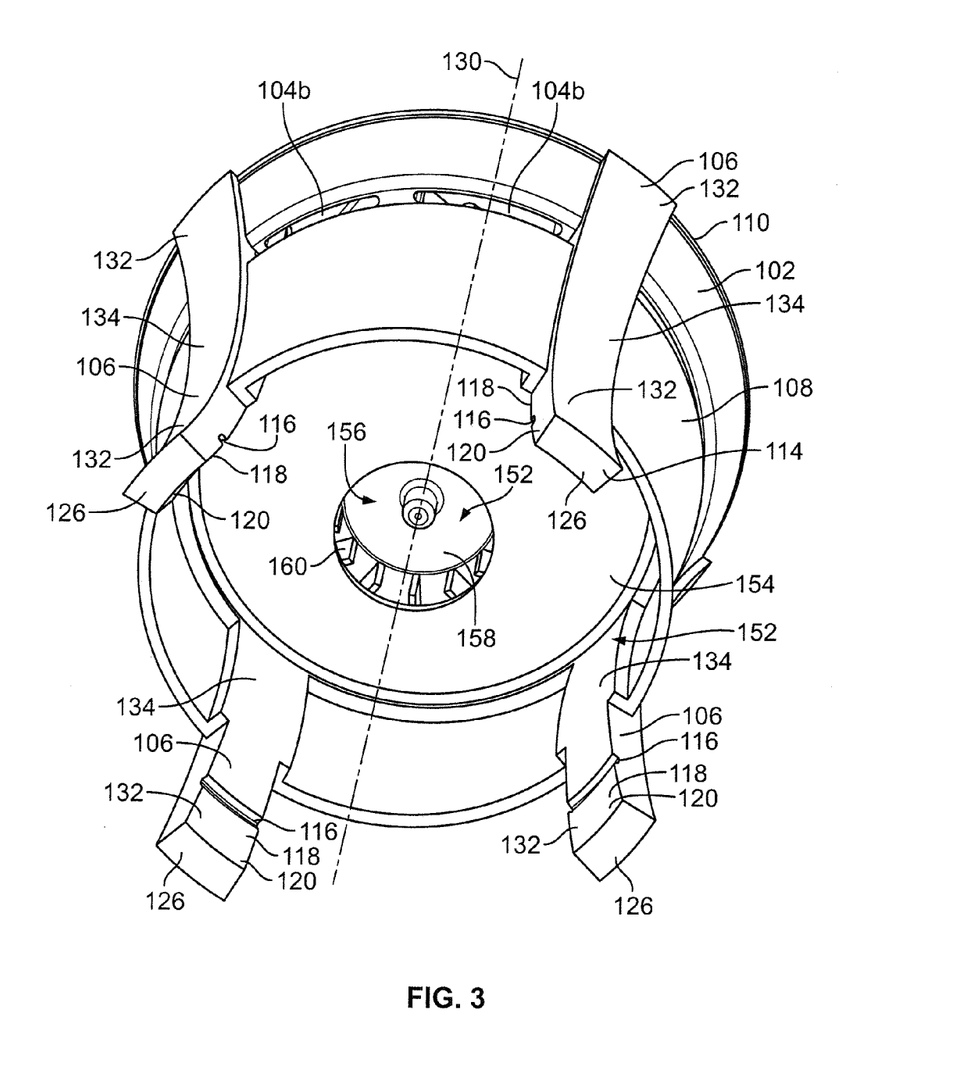
FIG. 3 is an isometric view of a bottom, front, and side of the dispensing system of FIG. 1 with the refill unit removed therefrom for purposes of clarity.
Figure 4:
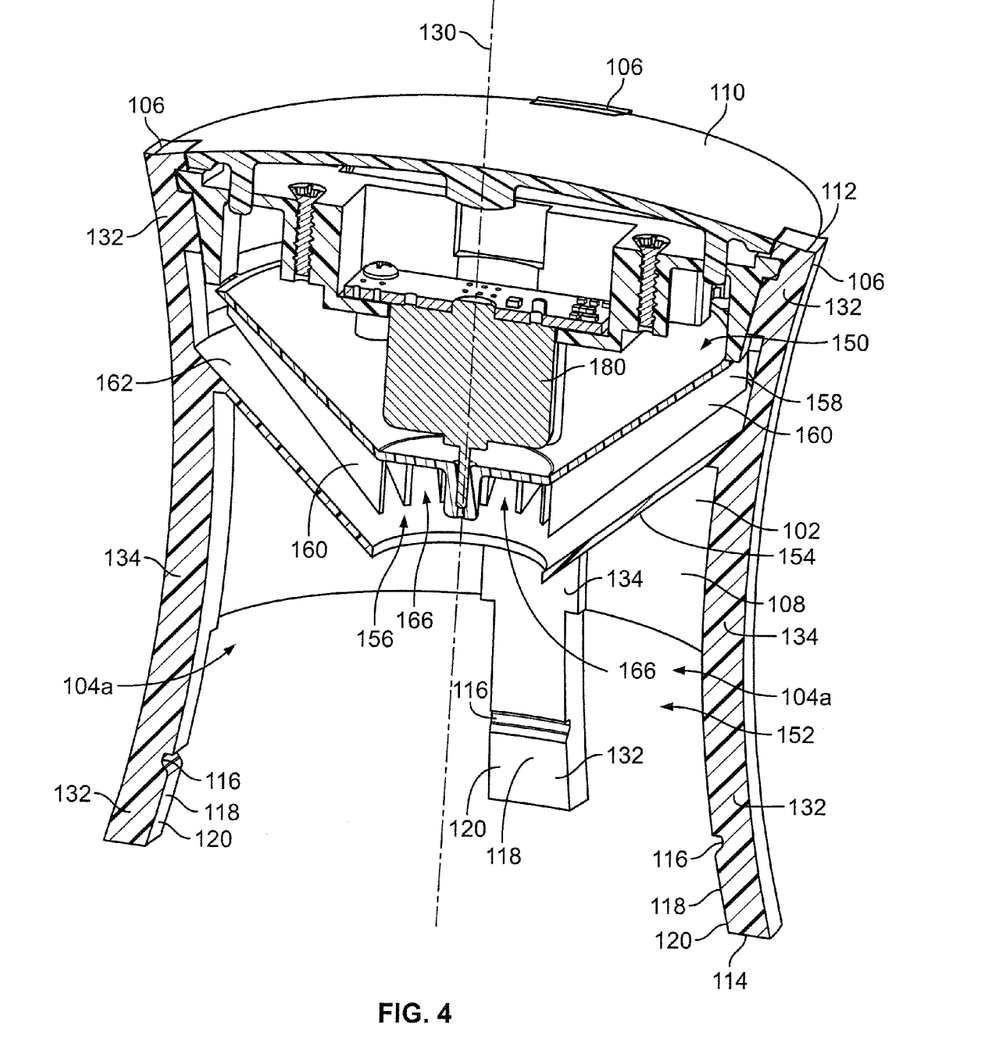
FIG. 4 is a cross-sectional view of the dispensing system of FIG. 3 taken generally along lines 4-4 of FIG. 1.

Still referring to FIGS. 1-4, the support members 106 extend downwardly from the end cap 110, bow slightly outwardly, and terminate adjacent a lower end 114 of the housing 102. As best seen in FIGS. 3 and 4, the support members 106 each include a groove 116 disposed on interior surfaces 118 of the support members 106 adjacent lower ends 120 thereof. The grooves 116 are adapted to receive correspondingly shaped portions of a volatile material refill unit 124, which is described in more detail hereinbelow. Bottom surfaces 126 of the support members 106 are substantially flat and adapted to correspond to a similarly angled bottom surface 128 (see FIG. 6) on the volatile material refill unit 124 to form a unitary base for the volatile material dispensing system 100 to rest in an upright position on a support surface (not shown).

The four support members 106 are disposed equidistantly around a central axis 130 of the housing 102 and are adapted to be spaced so as to maximize the airflow through the volatile material dispensing system 100. Although four support members 106 are shown, the housing 102 may include any number of support members so long as airflow through the system 100 is not substantially impeded.

The curvature of the support members 106 is defined by two curved end portions 132 integral with a small central portion 134 disposed adjacent the cylindrical sidewall 108. Each of the curved members 106 includes a radius of curvature of about 1 degree to about 90 degrees. In a different embodiment, the radius of curvature is about 20 degrees to about 70 degrees. In yet a different embodiment, the radius of curvature is about 25 degrees to about 35 degrees. Each of the curved members further include an arc length of about 100 mm to about 400 mm. In a different embodiment, the arc length is about 150 mm to about 250 mm. In another embodiment, the arc length is about 175 mm to about 200 mm.

The support members 106 are preferably resilient such that at least the lower ends 120 flex outwardly to allow the refill unit 124 to be inserted therein. Once the refill unit 124 is within the housing 102, preferably the support members 106 return to their original position to releasably engage the refill unit 124. The radius of curvature of the support members 106 may facilitate the degree of flexing that is appropriate for different types of refill units 124 and may be adapted in manners known in the art. Such flexing allows the user to insert and releasably lock the refill unit 124 into the housing 102.

As best seen in FIG. 4, the rectilinear grooves 116 are disposed in the lower ends 120 of the support members 106 and extend across the entire interior surface 118 of each of the support members 106 in a direction substantially transverse to the central axis 130 of the housing 102. In a different embodiment, the grooves 116 may extend only partially across the interior surfaces 118 and/or may be disposed in one or more of the support members 106. Although depicted as rectilinear, the grooves 116 may be shaped and sized in a manner to correspond to other structural attributes of the volatile material refill unit 124. The grooves 116 act as an attachment mechanism to snap-fit the volatile material refill unit 124 to the housing 102 in an operable position. In a different embodiment, the housing 102 may include other mechanisms to secure the volatile material refill unit 124 to the housing 102, such as, for example, an adhesive, magnets, an interference fit, and the like.

As best seen in FIG. 2, the elongate lower openings 104a are provided adjacent the support members 106 and allow access to interior portions of the housing 102. In particular, the lower openings 104a are provided to act as air intake openings such that ambient air is pulled into the volatile material dispensing system 100. The air travels through the volatile material dispensing system 100, interacts with the volatile material refill unit 124, and is expelled through the smaller upper vents 104b disposed adjacent the end cap 110 of the housing 102, the operation of which is described in further detail hereinbelow.

Sizing of both the lower openings 104a and the upper vents 104b, both individually and in relation to each other, is important to ensure proper airflow through the volatile material dispensing system 100. In particular, the lower openings 104a each preferably include a length dimension $L_1$ of between about 30 mm to about 70 mm and a height dimension $H_1$ of between about 10 mm to about 40 mm as depicted in FIG. 2. In a different embodiment, the length dimension is between about 40 mm to about 60 mm and a height dimension is between about 15 mm to about 35 mm. Similarly, the upper vents 104b each preferably include a length dimension $L_2$ of between about 10 mm to about 20 mm and a height dimension $H_2$ of between about 3 mm to about 10 mm. The ratio between the lower openings 104a and the upper vents 104b is preferably about 1:3. That is, there is one lower opening 104a that corresponds to approximately three upper vents 104b. However, air entering the lower openings 104a may exit through any upper vent 104b as will be described in more detail hereinbelow. In a different embodiment, the ratio of lower openings 104a to upper vents 104b is about 1:1, 1:2, 1:4, or any other ratio that facilitates airflow through the volatile material delivery system 100.

Now turning to FIGS. 3 and 4, the housing 102 is divided into an upper chamber 150 and a lower chamber 152 by a substantially conical wall 154 that extends downwardly into the housing 102. The conical wall 154 includes a centrally disposed circular orifice 156 that allows air from the lower chamber 152 to enter into the upper chamber 150. A fan 158 is provided within the upper chamber 150. The fan 158 includes a plurality of blades 160 that are disposed adjacent an upper surface 162 of the conical wall 154. The blades 160 define a plurality of air flow channels 166 that extend outwardly toward the sidewall 108 and terminate at the upper vents 104b. The plurality of channels 166 are substantially rectilinear and are spaced equidistantly around the orifice 156. In the embodiment depicted, the channels 166 (and conical wall 154) extend upwardly at about a 45 degree angle from the centrally disposed orifice 156. In other embodiments, the channels 166 and/or the conical wall 154 may extend at other angles, such as, for example, between about 10 degrees to about 80 degrees, more preferably between about 25 degrees to about 75 degrees, and most preferably between about 35 degrees to about 50 degrees. The channels 166 are preferably aligned to minimize resistance to the airflow through the housing 102. It is envisioned that the channels 166 and the conical wall 154 may be angled differently according to the geometry and size of both the lower openings 104a and the volatile material refill unit 124 to maximize airflow through the entire volatile material dispensing system 100.

Figure 11:
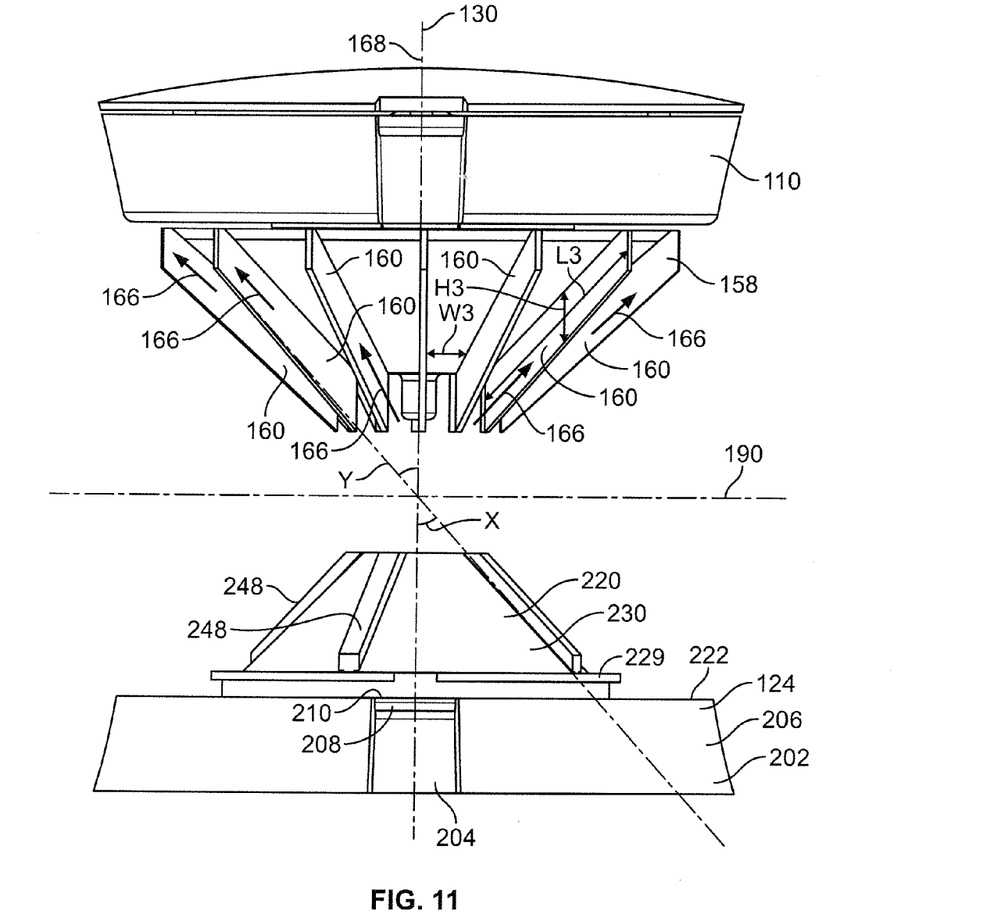
FIG. 11 is a side elevational view of the volatile material dispensing system of FIG. 1 with portions of the housing removed for clarity.

As best seen in FIG. 11, the channels 166 include a length dimension $L_3$ of about 20 mm to about 50 mm, a height dimension $H_3$ of about 2 mm to about 15 mm, and a width dimension $W_3$ of about 2 mm to about 20 mm. In a different embodiment, the channels 166 include a length dimension of about 30 mm to about 40 mm, a height dimension of about 4 mm to about 12 mm, and a width dimension of about 4 mm to about 15 mm. In still a further embodiment, the channels 166 include a length dimension of about 31 mm to about 35 mm, a height dimension of about 5 mm to about 8 mm, and a width dimension of about 6 mm to about 10 mm.

Still referring to FIGS. 1-4, the fan 158 is preferably a mixed flow fan that is provided in the upper chamber 150 of the housing 102 in an inverted position. Mixed flow fans are particularly preferred because air is pulled into the lower openings 104a in a manner substantially coincident with an axis 168 of the fan 158 (see FIG. 11), which in the present embodiment is also coincident with the central axis 130 of the housing 102. Air is drawn over the volatile material refill unit 124 in a manner that provides a path of least resistance for the air. The air is sent through the channels 166 and dispensed out of the upper vents 104b.

The fan 158 is preferably propelled between about 100 RPMs and about 4,000 RPMs and, more preferably, between about 200 RPMs and 600 RPMs. Further, the fan 128 has between about 12 and about 16 blades 160 and, preferably, between about 13 and about 15 blades 160, and most preferably about 14 blades. Although the plurality of blades 158 are shown as straight, it is contemplated that curved blades may also be used.

As best seen in FIG. 4, a drive mechanism 180 is disposed adjacent the fan 158 and connected thereto. The drive mechanism 180 is provided in the form of a motor and is adapted to supply energy to the fan 158 to promote airflow through the volatile material dispensing system 100. One suitable motor is a Mabuchi Motor, Model RF-330TK (Japan). In other embodiments, it is contemplated that other motors may be used to supply rotational movement to the fan 158.

A power mechanism (not shown) is disposed adjacent the end cap 110 and preferably supplies electrical power to the drive mechanism 180, which in turn operates the fan 158. In one embodiment, the power mechanism comprises batteries (not shown). In a different embodiment, it is contemplated that the power mechanism may comprise a cord with electrical prongs extending therefrom (not shown) or any other mechanism that provides electrical power to the volatile material dispensing system 100.

One advantageous feature of the design of the volatile material dispensing system 100 is that the system is energy efficient. In particular, some dispensing systems known in the prior art utilize significant amounts of power in use. In contrast, the volatile material dispensing system 100 typically uses less than about 50 mW of energy per duty cycle, more preferably less than about 30 mW, and most preferably less than about 20 mW. A typical duty cycle of the volatile material dispensing system 100 comprises the fan 158 in an active state for approximately 40 seconds, and in an off position for approximately 60 seconds. However, it is contemplated that other duty cycles may be used depending on the application and desired output of the volatile material dispensing system 100.

Now turning to FIGS. 1 and 2, the refill unit 124 is shown inserted into the housing 102 and disposed adjacent the lower end 114. With reference to FIGS. 5-9, the refill unit 124 comprises a substantially circular base 202 that is interrupted by a plurality of stepped recesses 204 disposed in a sidewall 206 thereof. Each recess 204 is substantially rectangular and includes an overhang 208 along a top edge 210 thereof. The recesses 204 are adapted to receive portions of the support members 106 to retain the refill unit 124 in the housing 102. In particular, the rectilinear grooves 116 disposed in the lower ends 120 of the support members 106 are shaped to receive the corresponding overhang 208 of each recess 204. The shape and size of both the grooves 116 of the support members 106 and the overhang 208 of the recesses 204 may be different so long as they act in conjunction to releasably retain the refill unit 124 in the housing 102. When the refill unit 124 is disposed within the housing 102, portions of the support members 106 adjacent the lower ends 120 are provided within the recesses 204 and the corresponding overhang 208 is recessed in the grooves 116 of the support member 106. Although an overhang 208/groove 116 snap-fit system is shown, it is contemplated that the refill unit may be releasably retained by the housing in various manners such as an interference fit, a releasable adhesive, magnets, and/or any other mechanism that acts to retain the refill unit 124 in the housing 102.

Still referring to FIGS. 5-8, the refill unit 124 includes a truncated conical wicking surface 220 that extends from a top plate 222 of the base 202. The top plate 222 may be integral or otherwise attachable to the base 202. A cap 224 may be optionally placed over the wicking surface 220 (see FIG. 7) and is releasably disposed thereon to retain volatile material 226 (see FIG. 8) within the refill unit 124 prior to use. The cap 224 is adapted to cover the wicking surface 220 during non-use of the volatile material dispensing system 100 and should be removed prior to use. The cap 224 includes projections (not shown) that interact with an undercut 228 of a raised wall 229 on the top plate 222 to retain the cap 224 thereon. The cap 224 may be retained on the refill unit 124 in any manner known in the art so long as the cap 224 substantially seals the volatile material 226 within the refill unit 124. The refill unit 124 may be provided with the volatile material dispensing system 100 already inserted into the housing 102 or may be provided separately. While an integral refill unit 124 and housing 102 is contemplated, preferably the refill unit 124 is removable so that it may be replaced when the volatile material 226 has been used up.

The conical wicking surface 220 includes an upper angled section 230 that extends downwardly toward the top plate 222 of the refill unit 124, as seen in FIGS. 5, 6, 8, and 9. A secondary wicking surface 232 extends downwardly from the upper angled section 230 and is in fluid communication with a reservoir 234 of the refill unit (see FIG. 8) that retains the volatile material 226. The secondary wicking surface 232 is presently depicted as substantially vertical, but may be angled and/or comprise multiple depending portions extending from or adjacent to the wicking surface 232.

Figure 5:
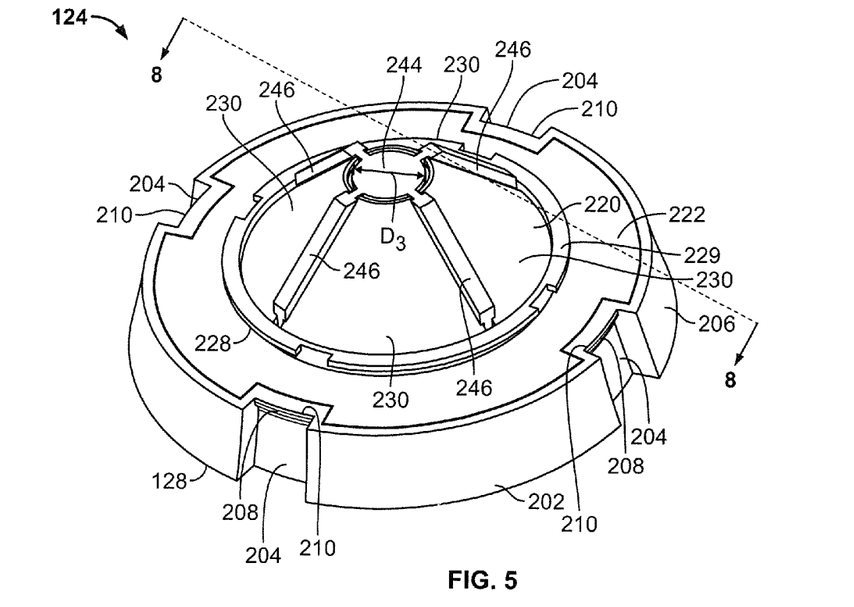
FIG. 5 is an isometric view of a top, front, and side of a volatile material refill unit.
Figure 6:
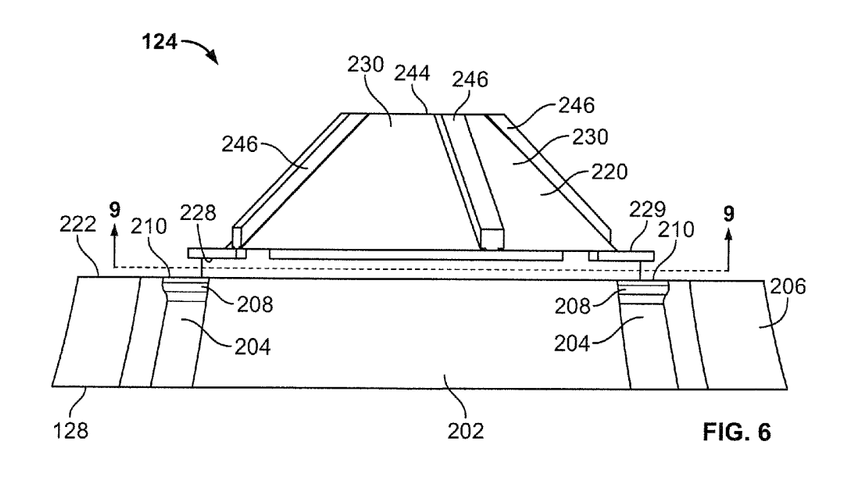
FIG. 6 is a side elevational view of the refill unit of FIG. 5.
Figure 7:
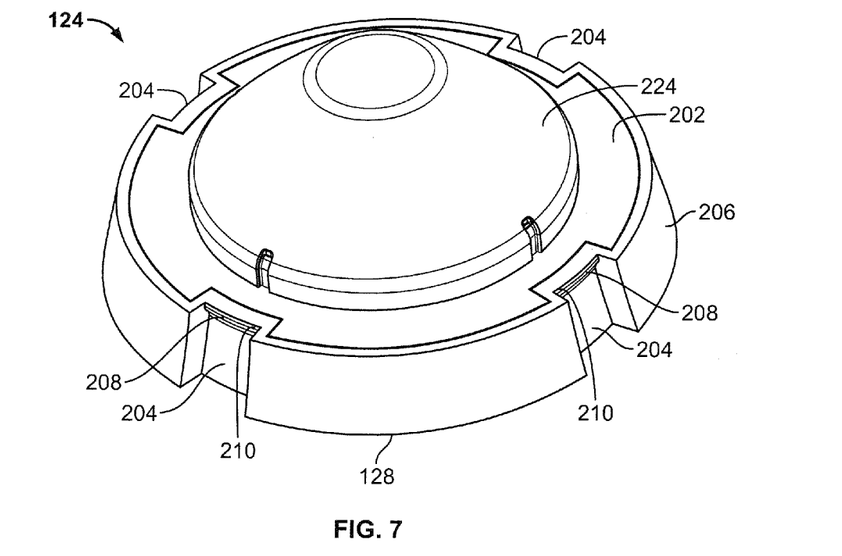
FIG. 7 is a isometric view of a top, front, and side of the volatile material refill unit of FIG. 5 further including a cap disposed thereon.
Figure 8:
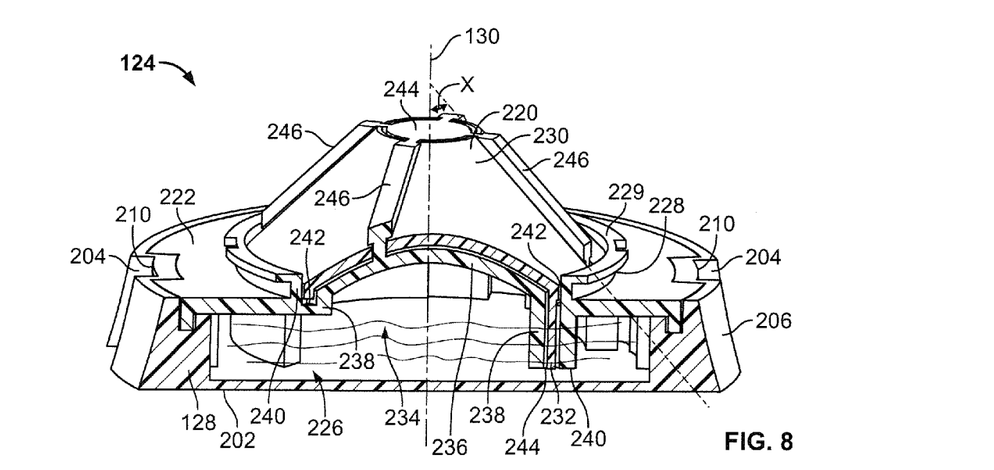
FIG. 8 is a cross-sectional view of the refill unit of FIG. 5 taken generally along lines 8-8 of FIG. 5.

Still referring to FIGS. 5, 6, and 8, the wicking surface 220 is supported by and disposed on a similarly shaped angled wall 236 of the base 202. In the present embodiment the angled wall 236 is conical in shape and comprises a central portion of the top plate 222. The wicking surface 220 is substantially hollow and defines a cavity within an interior that corresponds to the shape of the conical wall 236. Outer peripheral portions of the angled wall 236 define an interior sidewall 238 and portions of the raised wall 229 define an exterior sidewall 240. The interior sidewall 238 and the exterior sidewall 240 form a trough 242 therebetween that is adapted for receipt of portions of the wicking surface 220. In the present embodiment, a distal annular portion of the upper angled section 230 is received within the trough 242. Further, at least one opening 244 is provided within the trough 242, wherein at least one secondary wicking surface 232 extends therethrough and into the reservoir 234.

Figure 9:
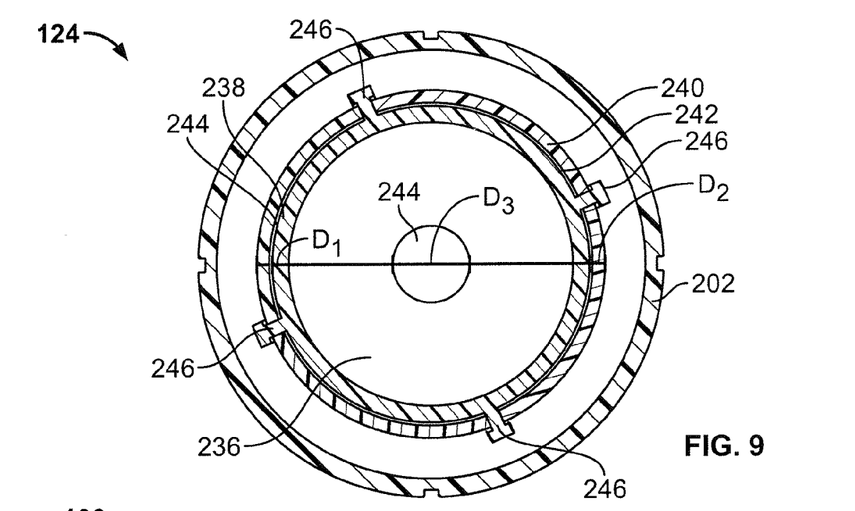
FIG. 9 is a cross-sectional view of the refill unit of FIG. 5 taken generally along lines 9-9 of FIG. 6.

The opening 244 is formed due to the interior sidewall 238 having a first diameter D1 and the exterior sidewall 240 having a second diameter D2 (see FIG. 9). Preferably, the first diameter D1 is smaller than the second diameter D2 such that the opening 244 is defined as the distance of D2–D1. The secondary wicking surface 232 extends downwardly between the interior sidewall 238 and the exterior sidewall 240, through the opening 244, and terminates within the reservoir 234 of the refill unit 124 (see FIG. 8). In one embodiment, a plurality of openings 244 are provided to allow a plurality of secondary wicking surfaces 232 to extend into the reservoir 234. The secondary wicking surface 232 preferably extends into the reservoir 234 of the refill unit 124 to a sufficient degree to interact with the volatile material 226 that is disposed therein. As the volatile material 226 contacts the secondary wicking surface 232, the volatile material 226 is transmitted from the reservoir 234, up the secondary wicking surface 232, and onto the upper angled section 230 of the wicking surface 220.

With reference to FIGS. 5, 6, 8, and 9, the angled wall 236 further includes a flat circular top end 246 having a third diameter D3 and a plurality of T-shaped rectilinear members 248 extending therefrom that segment the wicking surface 220 into four distinct sections. The T-shaped rectilinear members 248 are used to space the cap 224 from the wicking surface 220 prior to use. Although four rectilinear members 248 are shown, the rectilinear members 248 may be omitted all together or included in any number.

The wicking surface 220 is preferably made from polymers, polyolefins, nylons, cellulosics, other fibers, blends, and the like. In other embodiments, the wicking surface 220 comprises blends of polyethylene and polyester. Suitable wicking surfaces 220 may be any porous polymer fibers, such as the PE/PET fiber blend obtained from POREX® Corporation (Fairburn, Ga.). Another suitable wicking surface 220 is a polymeric fiber blend available from Filtrona Porous Technologies (Colonial Heights, Va.). The wicking surface 220 may be integral with the angled wall 236 or may comprise separate components. For example, the wicking surface 220 may be manufactured separately and adhered to the angled wall 236 in manners known in the art, e.g., an adhesive may be used. In other embodiments, the wicking surface 220 is made integral with the angled wall 236 during the manufacturing process.

In an alternative embodiment, the wicking surface 220 may comprise a cartridge (not shown) that includes a fragrance laden gel. The cartridge may be recessed in a cavity in the angled wall 236 such that the permeable membrane is flush with the surface of the angled wall 236. In one example, the cartridge includes an impermeable cup-shaped structure and a permeable membrane over the cup-shaped structure that acts as a sealed reservoir to contain a volatile material. The volatile material cartridge may further include an impermeable laminate that is adhered to the permeable membrane to substantially prevent diffusion of the volatile material therethrough. In one example, the volatile material cartridge is similar or identical to those described in U.S. Pat. No. 7,213,770 and U.S. Pat. No. 7,665,238. In use, the impermeable laminate is pealed from the volatile material cartridge and the cartridge is inserted into the cavity with the cup-shaped structure adjacent the reservoir 234 and the permeable membrane adjacent the surface of the angled wall 236.

The upper angled section 230 of the wicking surface 220 preferably includes a total surface area of about 10 to about 50 cm$^2$, and more preferably about 15 to about 35 cm$^2$, and most preferably about 30 cm$^2$. The surface area of the wicking surface 220 may be increased or decreased to accommodate different types of volatile materials.

As best seen in FIG. 8, the wicking surface 220 is angled with respect to the central axis 130. In the present embodiment, a central axis of the reservoir 234 and the wicking surface 220 is coincident with the central axis 130. In one embodiment, the angle X of the upper section 230 of the wicking surface 220 with respect to the central axis 130 is preferably about 20 degrees to about 75 degrees, more preferably about 30 degrees to about 60 degrees, and most preferably about 45 degrees. The angle and the total surface area of the wicking surface 220 are preferably selected to facilitate air entering the volatile material dispenser 100 to contact the wicking surface 220, but at the same time, provide diminished resistance to the airflow movement as will be explained in more detail hereinbelow.

Figure 10:
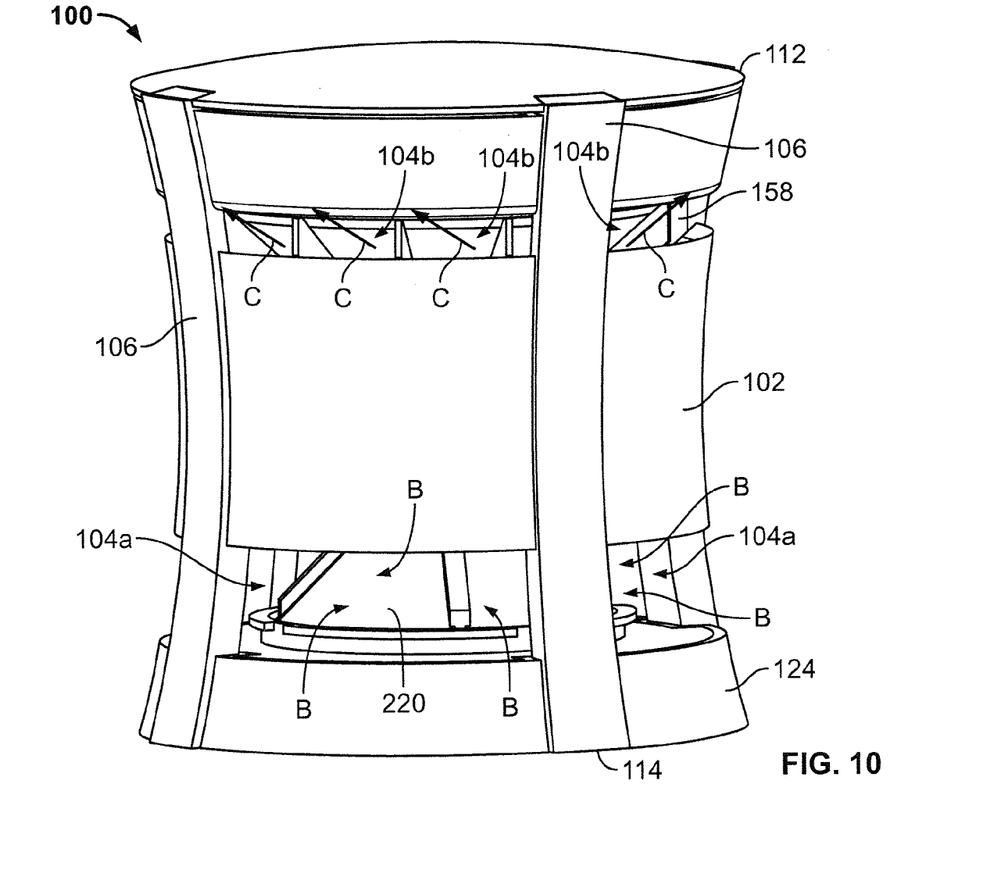
FIG. 10 is a different isometric view of a top, front, and side of a volatile material dispensing system depicted during operation showing exemplary air flow paths and including partial numbering for clarity.

Now referring to FIG. 10, air enters the housing 102 of the volatile material dispensing system 100 through the lower openings 104a as represented by exemplary flow paths depicted by arrows B. Air may enter the volatile material dispensing system 100 without the use of the fan 158, but it is preferable that the fan 158 is used during operation of the dispensing system 100 to facilitate airflow therethrough. In particular, the fan 158 is turned on by a power switch (not shown) that is electrically connected to the power mechanism and the drive mechanism 180, which in turn provides rotational movement to the fan 158. The fan 158 pulls or draws ambient air into the volatile material dispensing system 100 along its axis 168 through the lower openings 104a. The air contacts and flows along the wicking surface 220 and mixes with the volatile material 226. The volatile material laden, air is expelled from the volatile material dispensing system 100 through the upper vents 104b as shown by exemplary flow paths depicted by arrows C. The air is expelled from the volatile material dispensing system 100 at angles between about 25 degrees and about 70 degrees with respect to axis 130, as shown in FIGS. 8, 10, and 11.

The volatile material dispensing system 100 provides numerous advantages with respect to the angle of the wicking surface 220 and the airflow pattern through the volatile material dispensing system 100. In particular, the airflow of the present system flows along the wicking surface 220 as opposed to through or against the wicking structure as known in many prior art systems. The angling of the wicking surface in conjunction with the size, shape, and orientation of the lower openings 104a and upper vents 104b, and the use of a mixed flow fan 158, provides a path of least resistance to the air entering the system 100. The use of such parameters makes the system 100 significantly more energy-efficient than prior art systems and disperses the volatile material laden air out of the system 100 at an angle such that the radius of detection is magnified.

Many of the efficiencies of the volatile material dispensing system 100 are realized due to the geometry and angling of various components within the system 100. In particular, referring to FIG. 11, the angle X formed between the central axis 130 and the wicking surface 220 is substantially similar to an angle Y formed between the central axis 130 and the channels 166, which are aligned with the upper vents 104b (not shown in FIG. 11). In one embodiment, angles X and Y are approximately the same. In a different embodiment, angles X and Y are different. In one embodiment, angle X and angle Y with respect to the central axis 130 are preferably between about 20 degrees to about 75 degrees, more preferably about 30 degrees to about 60 degrees, and most preferably about 45 degrees.

The volatile material 226 may be a fragrance or insecticide disposed within a carrier liquid, a deodorizing liquid, or the like. For example, the volatile material may comprise OUST®, an air and carpet sanitizer for household, commercial, and institutional use, or GLADE®, a household deodorant, both sold by S. C. Johnson and Son, Inc., of Racine, Wis. The volatile material may also comprise other actives, such as sanitizers, air fresheners, odor eliminators, mold or mildew inhibitors, insect repellents, and the like, or that have aromatherapeutic properties. The volatile material alternatively comprises any volatile material known to those skilled in the art that can be dispensed from a housing.

Any of the embodiments described herein may be modified to include any of the structures or methodologies disclosed in connection with different embodiments. Further, the present disclosure is not limited to housing shapes/sizes of the type specifically shown. Still further, the housing of any of the embodiments disclosed herein may be modified to work with any type of volatile material refill unit using the disclosure herein.

All documents cited in the Detailed Description of the Invention are, in relevant part, incorporated herein by reference; the citation of any document is not to be construed as an admission that it is prior art with respect to the present invention.

INDUSTRIAL APPLICABILITY

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A volatile material dispensing system, comprising:
a housing and a refill unit, wherein the refill unit includes a volatile material and a wicking surface; and
a fan disposed within the housing,
wherein during an active state the fan draws ambient air into the housing and over the wicking surface, which is angled between about 20 degrees to about 75 degrees relative to a central axis of the housing, and
wherein during the active state the drawn air is expelled from the housing through channels of the fan at an angle of between about 20 degrees to about 75 degrees relative to the central axis of the housing.

2. The volatile material dispensing system of claim 1, wherein the wicking surface and the channels of the fan are provided at substantially equal angles to one another about the central axis.

3. The volatile material dispensing system of claim 2, wherein the wicking surface and the channels of the fan are provided at a substantially 45 degree angle with respect to the central axis.

4. The volatile material dispensing system of claim 1, wherein the ambient air is drawn through a plurality of lower openings disposed adjacent a lower end of the housing and expelled through a plurality of upper vents disposed adjacent an upper end of the housing.

5. The volatile material dispensing system of claim 1, wherein the fan is a mixed flow fan.

6. The volatile material dispensing system of claim 1, wherein the housing comprises four elongate support members.

7. The volatile material dispensing system of claim 1, wherein the central axis of the housing is coincident with a central axis of the fan.

8. A refill unit for a volatile material dispensing system, comprising:
a reservoir holding a volatile material; and
a wicking surface having a first upper angled section and a secondary wicking surface extending downwardly therefrom into the reservoir,
wherein the upper angled section is angled from between about 20 degrees to about 75 degrees from a central axis of the reservoir, and
wherein the secondary wicking surface is substantially parallel to the central axis of the reservoir.

9. The refill unit of claim 8, wherein the upper angled section comprises a truncated conical shape.

10. The refill unit of claim 9, wherein the upper angled section includes a flat top end.

11. The refill unit of claim 8, wherein the upper angled section is angled from between about 30 degrees to about 60 degrees.

12. The refill unit of claim 11, wherein the upper angled section is angled about 45 degrees.

13. The refill unit of claim 8, wherein the upper angled section has a surface area of between about 15 cm² to about 35 cm².

14. A refill unit for a volatile material dispensing system, comprising:
- a base having a sidewall and a top plate;
- a reservoir within the base containing a volatile material;
- at least two opposing grooves within the sidewall, wherein portions of the sidewall defining the grooves include an overhang portion for snap-fit receipt within a housing; and
- a wicking surface including a first wicking section angled with respect to a secondary wicking section in fluid communication with the reservoir.

15. The refill unit of claim 14, wherein the top plate is integral with the sidewall.

16. The refill unit of claim 14, wherein an angled wall extends from the top plate and the first wicking section is disposed thereon.

17. The refill unit of claim 16, wherein a peripheral portion of the angled wall defines an interior sidewall and portions of a raised wall on the top plate define an exterior sidewall.

18. The refill unit of claim 17, wherein a trough is defined between the interior sidewall and the exterior sidewall that is sized to receive portions of the first wicking section.

19. The refill unit of 18, wherein at least one opening extends through portions of the top plate defining the trough, wherein the secondary wicking section extends therethrough.

20. The refill unit of claim 19, wherein a plurality of second wicking sections extends through a corresponding plurality of openings.

* * * * *